US008883076B2

(12) United States Patent
Somma et al.

(10) Patent No.: US 8,883,076 B2
(45) Date of Patent: Nov. 11, 2014

(54) APPARATUS AND PROCESS FOR RECYCLING ABSORBENT SANITARY PRODUCTS

(71) Applicant: FATER S.p.A., Pescara (IT)

(72) Inventors: Marcello Somma, Pescara (IT); Giorgio Vaccaro, Pescara (IT); Jan K. Michalek, Pataskala, OH (US); Theodore Thomas, Columbus, OH (US)

(73) Assignee: FATER S.p.A., Pescara (IT)

( * ) Notice: Subject to any disclaimer, the term of this patent is extended or adjusted under 35 U.S.C. 154(b) by 186 days.

(21) Appl. No.: 13/686,818

(22) Filed: Nov. 27, 2012

(65) Prior Publication Data
US 2013/0146690 A1 Jun. 13, 2013

(30) Foreign Application Priority Data

Nov. 28, 2011 (IT) .............. TO2011A1089

(51) Int. Cl.
A61L 2/08 (2006.01)
A61L 2/00 (2006.01)
F01B 11/02 (2006.01)
B02C 17/00 (2006.01)
A61L 2/07 (2006.01)
B02C 17/18 (2006.01)

(52) U.S. Cl.
CPC ................. B02C 17/1815 (2013.01); A61L 2/07 (2013.01)
USPC ................... 422/33; 422/1; 422/26; 422/295; 422/297; 422/305; 92/171.1; 241/15; 241/23; 241/24.19

(58) Field of Classification Search
CPC ............. A61L 2/00; A61L 2/07; A61L 9/03; A61L 11/00; B09B 3/00; B09B 3/0075
USPC ......... 422/1, 26, 33, 295, 297, 300, 305, 307, 422/309; 261/83; 92/171.1; 241/15, 23, 241/24.19, 25
See application file for complete search history.

(56) References Cited

U.S. PATENT DOCUMENTS 5,116,363 A * 5/1992 Romweber et al. ............. 34/443
5,292,075 A   3/1994 Bartlett
6,241,953 B1  6/2001 Krijgsman

FOREIGN PATENT DOCUMENTS

| JP | 2004113915 A | 4/2004 |
|----|--------------|--------|
| WO | 9420668 A1   | 9/1994 |
| WO | 9627045 A1   | 9/1996 |
| WO | 9926720 A1   | 6/1999 |
| WO | 0168152 A2   | 9/2001 |
| WO | 2006056768 A2| 6/2006 |
| WO | 2010065088 A1| 6/2010 |

OTHER PUBLICATIONS

Italian search report for application No. TO20111089 dated Apr. 10, 2012.

* cited by examiner

Primary Examiner — Monzer R Chorbaji
(74) Attorney, Agent, or Firm — Patterson & Sheridan, L.L.P.

(57) ABSTRACT

An apparatus for treating used absorbent sanitary products, comprising, a rotary cylindrical autoclave having an inner surface and two ends, at least one of which terminates in a hatch that can be opened to enable access to said autoclave and sealably closed to enable pressurization of said autoclave; and a circuit for heating and pressurizing the autoclave for heating the absorbent sanitary products to a sterilization temperature, wherein said autoclave comprises a sealing layer on said inner surface, designed to prevent adhesion on said inner surface of material coming from destructuring of said absorbent sanitary products.

5 Claims, 3 Drawing Sheets

APPARATUS AND PROCESS FOR RECYCLING ABSORBENT SANITARY PRODUCTS

CROSS-REFERENCE TO RELATED APPLICATIONS

This application claims benefit of Italian Patent Application No. TO2011A001089, filed Nov. 28, 2011, which is herein incorporated by reference.

BACKGROUND OF THE INVENTION

1. Field of the Invention

The present invention relates to an apparatus and a process for recycling used absorbent sanitary products.

By the term "absorbent sanitary products" is meant in general disposable absorbent products, such as: baby diapers, incontinence absorbent pads, ladies sanitary pads, bed mats, etc.

2. Description of the Related Art

Absorbent sanitary products are generally made up of a wide range of different materials, amongst which sheets of plastic material, cellulose fluff, superabsorbent polymers, sheets of non-woven fabric, etc.

Absorbent sanitary products contain high-quality materials such as plastic and cellulose, and it would be desirable to recover said materials to use them in a new production cycle or else for the production of energy.

Currently, used absorbent sanitary products are disposed of as undifferentiated waste to be sent to rubbish dumps. The component materials of used absorbent sanitary products are not recovered in the first place because the various materials (cellulose fibres, superabsorbent polymers, sheets of plastic material, etc.) are intimately interconnected, and to obtain separation of the materials it would be necessary to carry out a complete destructuring of the products. In addition, used absorbent sanitary products contain organic excretions and bacteria, and it would be necessary to carry out a sterilization of the products prior to recycling of the materials.

For the above reasons, used absorbent sanitary products are not included amongst recyclable waste products for which differentiated collection is carried out.

It is estimated that absorbent sanitary products constitute approximately 2-3% of the total of urban solid waste. However, where a differentiated collection is carried out with a high percentage of differentiation of the waste (with a percentage of differentiated waste higher than 60% of the total) the percentage of absorbent sanitary products with respect to the remaining part constituted by the undifferentiated residual fraction rises to approximately 20%.

The high percentage of absorbent sanitary products with respect to the residual fraction of non-recyclable waste renders highly desirable the availability of equipment and processes that enable a treatment of absorbent sanitary products to be carried out aimed at recycling their component materials in an efficient and economically convenient way.

Currently known techniques for treatment of used absorbent sanitary products are not satisfactory. A first known technique envisages carrying out washing of the used absorbent products with water, alkalis, and soap and separating the cellulose from the plastic during the washing operation. Examples of this technique are disclosed in the documents Nos. WO 94/20668 and WO 96/27045.

The document No. U.S. Pat. No. 5,292,075 describes a process in which the dirty absorbent sanitary products are preliminarily shredded. The shredded material is then washed in a washing machine comprising a perforated cylindrical drum that withholds the plastic material inside it. The material containing the cellulose pulp is then dehydrated.

These techniques of treatment of absorbent sanitary products are in actual practice problematical to implement since the washing water would contain a high amount of pollutants, such as gelified superabsorbent polymers and organic residue, which renders problematical disposal thereof. Drying of the cellulose after washing moreover entails a high expenditure of energy.

A further difficulty derives from the fact that used absorbent sanitary products are normally thrown away folded and closed to form a pack, with the outer plastic layer of the products that forms an impermeable barrier. If the products are treated in the form in which they have been thrown away, the outer impermeable layer prevents an effective sterilization of the products. On the other hand, a preliminary treatment as described in U.S. Pat. No. 5,292,075 entails the need to shred articles with a high content of organic excretions, bacteria, and contaminants.

The document No. JP 2004113915 describes a process for treating diapers that contain absorbent polymers, whereby the used diapers are set in a pressurized closed vessel together with sawdust. Inside the vessel the diapers are treated with steam at high temperature and high pressure for a pre-set time. Steam treatment is carried out at a pressure of 15-25 atm and at a temperature of 150-250° C. This document envisages use of the absorbent sanitary products, after said treatment, as fertilizers following upon fermentation.

The document No. WO 2010/065088 describes an autoclave for the treatment of urban solid waste that envisages drying of the waste using steam. The apparatus described in the document WO 2010/065088 comprises a rotary cylindrical autoclave provided with at least one hatch that can be opened to enable access to the autoclave and sealably closed to enable pressurization of the autoclave, an inlet for contact steam that comes into direct contact with the waste contained inside the autoclave, a plurality of straight hollow blades, which are designed to conduct non-contact steam, project from the inner surface of the autoclave, and are supplied with non-contact steam. This apparatus enables sterilization of urban solid waste and drying of the waste during treatment in the autoclave. The apparatus described in the document WO 2010/065088 has been developed for treatment of undifferentiated urban solid waste and does not contains specific teachings to obtain sterilization, drying, and separation of the component materials of absorbent sanitary products.

SUMMARY OF THE INVENTION

The object of the present invention is to provide an apparatus and a process for treating used absorbent sanitary products that will enable sterilization, drying, and destructuring of used absorbent sanitary products in order to carry out recovery of the constituent materials.

According to the present invention, the above object is achieved by an apparatus and a process having the characteristics forming the subject of claims 1 and 2, respectively.

The claims form an integral part of the teaching provided herein in relation to the invention.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

Figure 1:
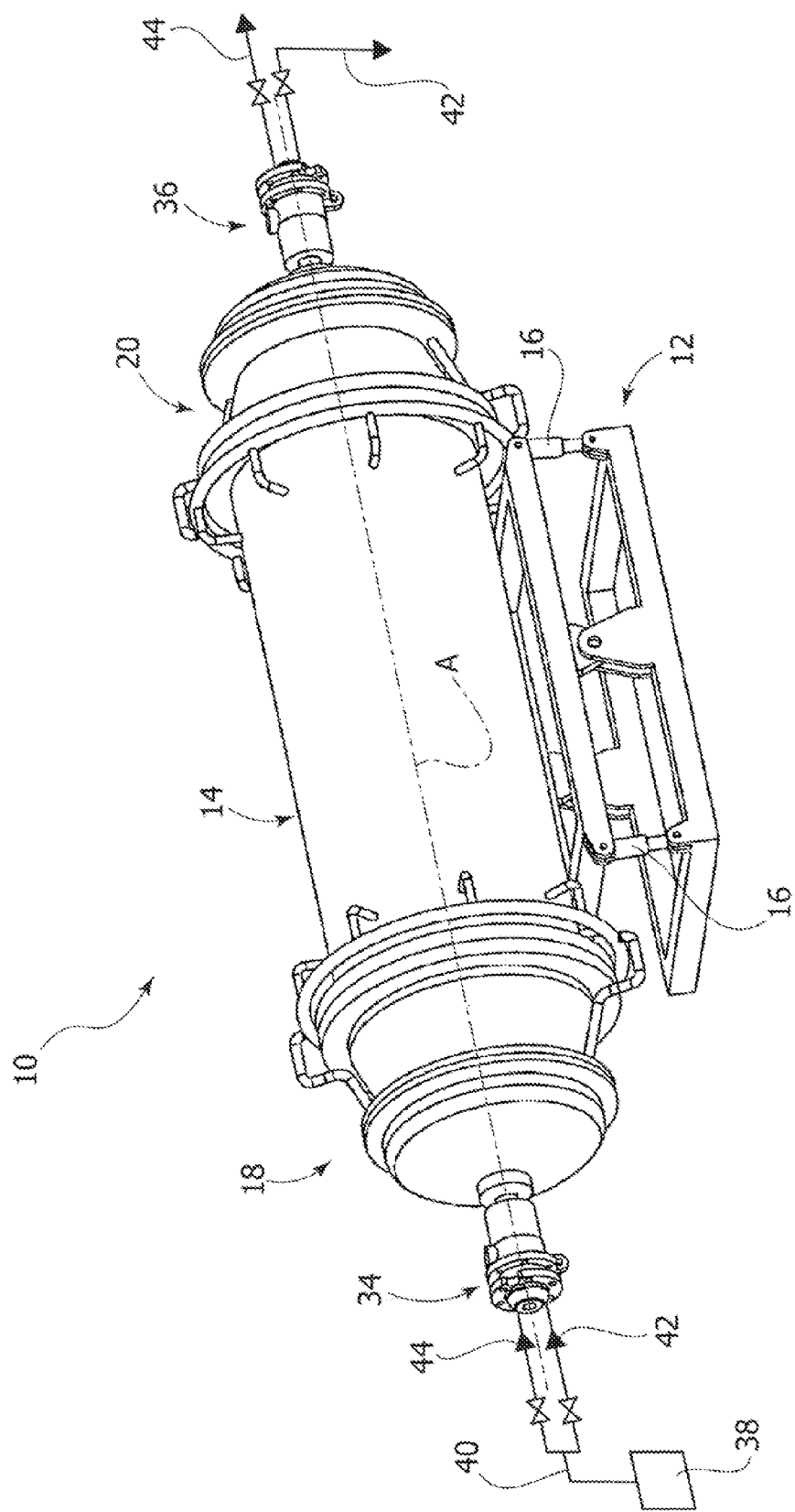
FIG. 1 is a perspective view of a rotary-autoclave apparatus for treating waste.

With reference to FIG. 1, designated by 10 is a rotary-autoclave apparatus for treating used absorbent sanitary products. The apparatus 10 comprises a stationary structure 12, which carries a cylindrical autoclave 14 that turns about its longitudinal axis A. The apparatus 10 comprises a driving device (not illustrated), which drives the autoclave 14 in rotation about the axis A. The supporting structure 12 may be provided with actuators 16 for varying the inclination of the autoclave 14 with respect to a horizontal axis, which enables tilting of the autoclave 14 between a loading/unloading position and a working position. The autoclave 14 has two ends, at least one of which terminates in a hatch that can be opened to enable access to the internal space of the autoclave and sealably closed to enable pressurization of the internal space. In the example illustrated two openable hatches 18, 20 are provided, which can be used, for example, for loading the autoclave with the products to be treated and for unloading the treated products. Alternatively, a single openable hatch could be provided, which can be used both for loading and for unloading.

The apparatus 10 comprises a circuit for heating and pressurizing the autoclave 14 in order to heat the absorbent sanitary products to a sterilization temperature.

Figure 2:
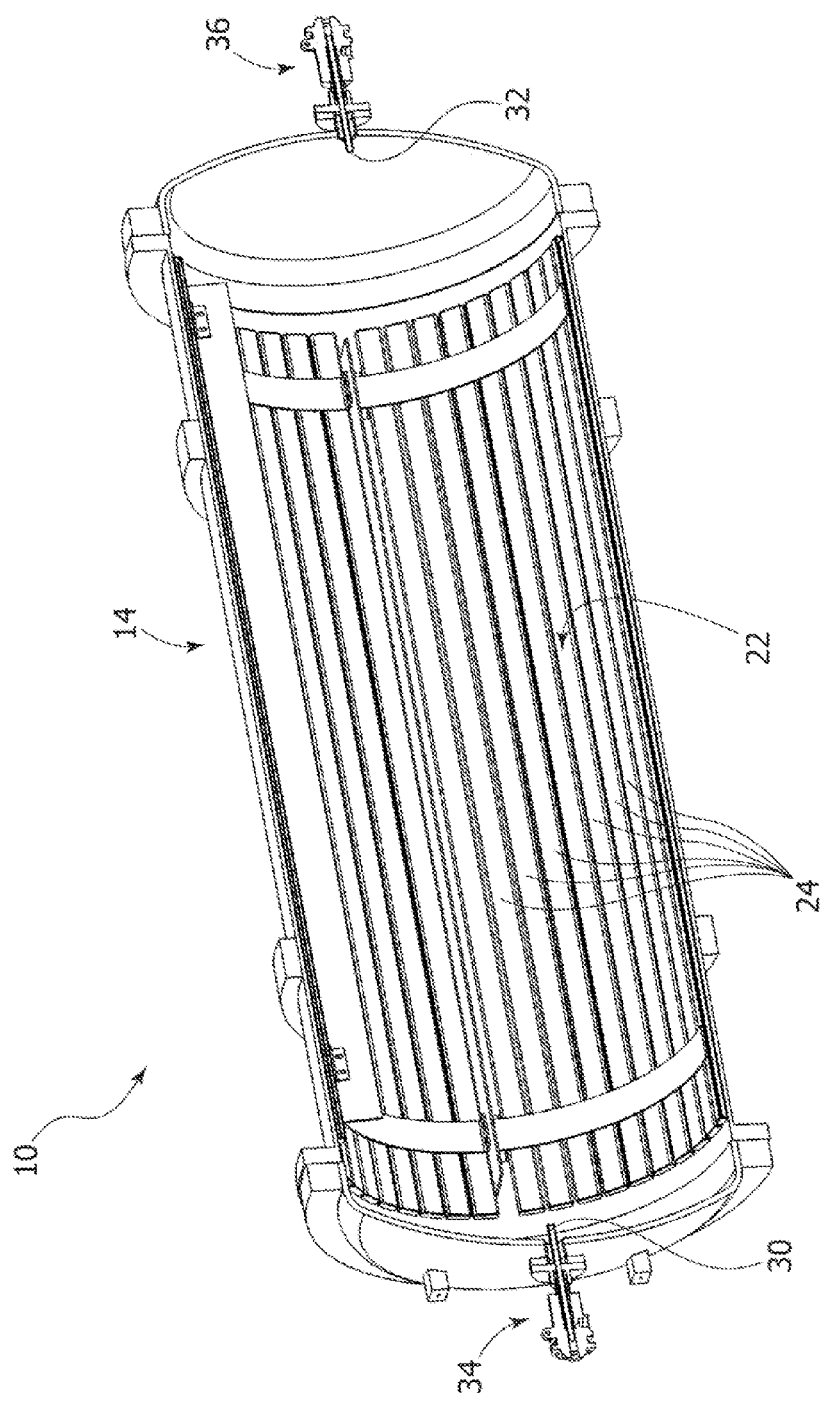
FIG. 2 is a sectioned perspective view of the autoclave of FIG. 1.

FIG. 2 is a schematic sectioned view of the autoclave 14. In FIG. 2 it may be noted that the autoclave 14 has an inner surface 22 that delimits a treatment volume. Arranged within the autoclave 14 is a plurality of ducts 24 that form a part of the inner surface 22. The ducts 24 extend parallel to the longitudinal axis A and are connected at their opposite ends to respective headers for inlet and outlet of heating steam. The steam that traverses the ducts 24 does not come into contact with the products to be treated contained in the internal volume of the autoclave 14 and is consequently referred to as "non-contact steam".

The hatches 18, 20 are provided with an inlet 30 and an outlet 32 for contact steam that comes into direct contact with the products set within the autoclave 14. The contact steam has the function of pressurizing the autoclave 14 and heating the products by direct contact. The hatches 18, 20 are provided with respective rotary connectors 34, 36, respectively, for entry and for exit of the contact steam and non-contact steam. As represented schematically in FIG. 1, the apparatus 10 comprises a steam generator 38, which produces a flow of steam 40 that is divided into a flow of non-contact steam 42 that traverses the ducts 24 and a flow of contact steam 44 that pressurizes the internal volume of the autoclave 14. On the outlet connector 36 the flow of non-contact steam 42 and the flow of contact steam 44 are divided and treated separately, for example as described in the document No. WO 2010/065088.

In operation, the autoclave 14 is loaded with absorbent sanitary products. The autoclave 14 is then sealably closed and pressurized by the contact steam. At the same time, the autoclave is heated by the non-contact steam present the ducts 24. The autoclave, once heated and pressurized, is driven in rotation about the axis A. After a pre-set period sufficient to obtain drying, destructuring, and sterilization of the products, the autoclave is opened, and the treated products are unloaded and sent on to a sieve, in which separation of the plastic from the cellulose is carried out.

Typically, absorbent sanitary products comprise an absorbent core of cellulose fibres and of superabsorbent polymers. The absorbent core is usually enclosed between two sheets of plastic material joined together. Typically, the backsheet is impermeable, whereas the topsheet is porous. Used absorbent sanitary products are normally folded up so as to enclose the product in the form of a pack within the impermeable backsheet. Usually adhesive tabs are provided for closing the folded product. The organic excretions are thus enclosed within a sealed sheet of impermeable plastic material.

The apparatus 10 according to the present invention envisages carrying out the treatment of absorbent sanitary products just as they are collected, i.e., in the form where they are closed to form a pack, and without any preliminary treatment for opening the products.

The temperature and pressure treatment combined with shaking inside the autoclave 14 performs drying, destructuring, and sterilization of the absorbent sanitary products. To obtain an effective action of drying and sterilization, it is necessary to obtain opening of the products so as to expose all the organic substances to the high temperature and to the contact steam in every point inside the autoclave 14.

Opening of the absorbent sanitary products is absolutely essential to obtain a complete sterilization. It has been found that low operating temperatures of the autoclave 14 are insufficient to produce opening of the products, whereas excessively high temperatures cause wrinkling of the topsheets of plastic material rendering separation problematical, which on the one hand jeopardizes the effectiveness of the sterilization process and on the other renders the material at output from the autoclave 14 unusable. It is only the use of intermediate temperatures that enables opening of the products but not destructuring thereof and that enables exposure of the cellulose fibres and the organic liquids absorbed thereby to the treatment. More precisely, it has been found that the plastic backsheets of absorbent sanitary products undergo wrinkling at temperatures higher than 150° C., whereas a temperature of approximately 138° C. is sufficient for melting the glue that keeps the absorbent sanitary products joined together, enabling opening of the products and optimal exposure to the action of sterilization of the contact steam. Moreover, temperatures higher than 140° C. enable destruction of plastic bags that may contain the absorbent sanitary products.

With a pressurized rotary autoclave with dual supply of steam, the non-contact steam within the ducts 24 can be used for creating hot points inside the autoclave, which damage and cause failure of the plastic covers of the absorbent sanitary products without causing wrinkling thereof. Said hot points create points of localized melting that open holes in the plastic covers and weaken the outer envelopes in such a way that the action of agitation inside the rotary autoclave causes breaking of the outer envelopes, destructuring of the products, and complete exposure of the absorbent cores to the contact steam. The absorbent cores formed by cellulose fibres and superabsorbent polymers are hence released from the enveloping plastic material.

It has been found experimentally that, when the contents of the absorbent sanitary products come into contact with the heated surface of the autoclave 14, a part of the material dries and tends to stick to the wall. In time, the thickness of the dried material that accumulates on the inner wall of the autoclave 14 reaches unacceptable levels, and it is necessary to carry out laborious operations of cleaning of the inner surface of the autoclave 14.

Figure 3:
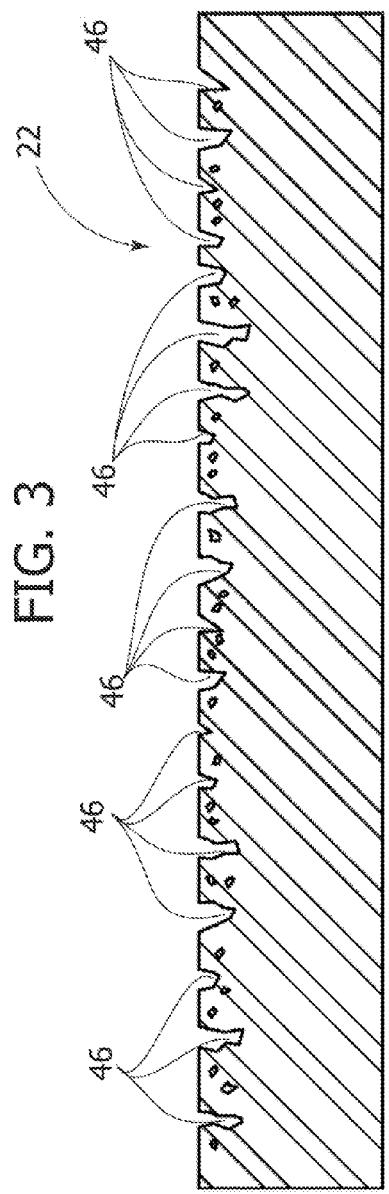
FIGS. 3 and 4 are schematic views that illustrate a detail of the inner surface of the autoclave of FIG. 2.
Figure 4:
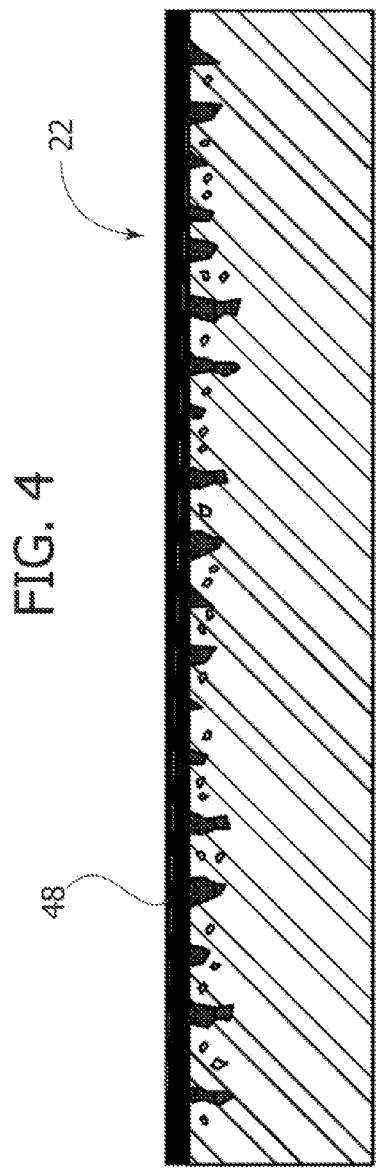

Adhesion of the material to the inner walls of the autoclave 14 during treatment of absorbent sanitary products is due to the presence on the inner surface 22 of micropores designated as a whole by 46 in FIG. 3. In order to reduce adhesion, it is necessary to reduce or eliminate the micropores 46.

There exists a wide range of ways to reduce the microporosity of a surface. One of these consists in forming a sealing layer 48 on the inner surface 22 of the autoclave 14. The sealing layer 48 fills the micropores 46 and prevents adhesion of material deriving from opening and tearing of the absorbent sanitary products.

The sealing layer 48 can be obtained with the application of grease or oil on the surface 22.

In one embodiment, the empty autoclave 14 is heated to a temperature higher than 150° C. with an addition of approximately 100 g of grease or oil per square meter of inner surface. This process is carried out with the autoclave empty. When the autoclave is cooled, the grease or oil in excess is removed, and there remains the sealing layer 48 that closes the micropores 46.

Alternatively, an amount of grease or oil of 10-100 g per square meter of the inner surface 22 is added to the load of absorbent sanitary products to be treated.

In operation, the temperature of the autoclave rises, and the lubricant comes into contact with the micropores 46 to form the sealing layer 48.

The oil or grease can be added as a solid, liquid, or aerosol. Also other types of sealants may be used. The essential feature of the invention consists in providing means for sealing the inner surfaces 22 of the autoclave 14 in such a way that contact adhesion with the material being treated will not occur.

The problem of adhesion of the material to the inner surface of the autoclave 14 does not arise during treatment of urban solid waste in an autoclave since in urban solid waste there is usually contained an amount of oil/grease sufficient to prevent adhesion of the material to the walls of the autoclave.

While the foregoing is directed to embodiments of the present invention, other and further embodiments of the invention may be devised without departing from the basic scope thereof, and the scope thereof is determined by the claims that follow.

The invention claimed is:

1. An apparatus for treating used absorbent sanitary products, comprising:

a rotary cylindrical autoclave having an inner surface and two ends, at least one of which terminates in a hatch that can be opened to enable access to said autoclave and sealably closed to enable pressurization of said autoclave; and a circuit for heating and pressurizing the autoclave for heating the absorbent sanitary products to a sterilization temperature, wherein said autoclave comprises a sealing layer on said inner surface, designed to prevent adhesion on said inner surface of material corning from destructuring of said absorbent sanitary products, wherein said sealing layer comprises grease or oil.

2. A process for treating used absorbent sanitary products, comprising the steps of:

providing a rotary cylindrical autoclave having an inner surface and two ends, at least one of which terminates in a hatch that can be opened to enable access to said autoclave and sealably closed to enable pressurization of said autoclave;

loading said autoclave with closed absorbent sanitary products;

heating to a sterilization temperature and pressurizing said autoclave and at the same time driving the autoclave in rotation about a longitudinal axis thereof; and forming a sealing layer on said inner surface of the autoclave by heating the autoclave and adding an amount of oil or grease, said sealing layer being designed to prevent adhesion to said inner surface of material corning from destructuring of said absorbent sanitary products.

3. The process according to claim 2, wherein formation of said sealing layer on said inner surface is carried out before loading said absorbent sanitary products.

4. The process according to claim 2, wherein formation of said sealing layer is carried out during treatment of said absorbent sanitary products by adding to the load of absorbent sanitary products an amount of oil or grease.

5. The process according to claim 2, wherein said amount of oil or grease is comprised between 10 and 100 g per square meter of the inner surface of the autoclave.

* * * * *

UNITED STATES PATENT AND TRADEMARK OFFICE
CERTIFICATE OF CORRECTION

PATENT NO. : 8,883,076 B2  
APPLICATION NO. : 13/686818  
DATED : November 11, 2014  
INVENTOR(S) : Somma et al.

Page 1 of 1

It is certified that error appears in the above-identified patent and that said Letters Patent is hereby corrected as shown below:

Claims:

Column 6, Claim 1, Line 14, please delete "corning" and insert --coming-- therefor;

Column 6, Claim 2, Line 33, please delete "corning" and insert --coming-- therefor.

Signed and Sealed this  
Twenty-eighth Day of April, 2015

Michelle K. Lee  
*Director of the United States Patent and Trademark Office*